United States Patent [19]

Taylor et al.

[11] Patent Number: 5,271,912

[45] Date of Patent: Dec. 21, 1993

[54] ENZYMATIC PROCESSING OF MATERIALS CONTAINING CHROMIUM AND PROTEIN

[75] Inventors: Maryann M. Taylor, Philadelphia, Pa.; Edward J. Diefendorf, Audubon, N.J.; Willian N. Marmer, Fort Washington; Eleanor M. Brown, Philadelphia, both of Pa.

[73] Assignee: The United States of America as represented by the Secretary of Agriculture, Washington, D.C.

[21] Appl. No.: 848,775

[22] Filed: Mar. 10, 1992

Related U.S. Application Data

[63] Continuation-in-part of Ser. No. 476,843, Feb. 8, 1990, Pat. No. 5,094,946.

[51] Int. Cl.$^5$ .................... C01G 37/00; C12P 21/06; C12J 7/00
[52] U.S. Cl. ........................ 423/55; 210/632; 210/913; 8/94.27; 435/265; 435/68.1
[58] Field of Search .................. 423/53, 54, 55, 57, 423/58, 607; 210/632, 913; 8/94.27; 435/265, 68.1

[56] References Cited

U.S. PATENT DOCUMENTS

| | | | |
|---|---|---|---|
| 4,100,154 | 7/1978 | Holloway | 260/123.7 |
| 4,332,584 | 6/1982 | Muralidhara | 8/94.27 |
| 4,483,829 | 11/1984 | Guardini | 423/55 |
| 5,094,946 | 3/1992 | Taylor et al. | 435/68.1 |

OTHER PUBLICATIONS

Chemical Abstracts vol. 115, No. 13 115:129420j (1991).
Taylor et al. "Enzymatic Treatment of Chrome Shoija" Journal of the American Leather Chemists association (Aug. 1990) pp. 264-275.
Taylor, Maryann, et al., "Enzymatic Treatment of Solid Waste Generated in the Tanning Industry," Abstracts of IVLTCS, 20th Congress, (Oct. 15-19, 1989).
Taylor, Maryann M., et al., "Enzymatic Treatment of Chrome Shavings," JALCA, vol. 84, p. 157, (May 1989).
Heidemann, E., "Disposal and Recycling of Chrome-Tanned Materials," JALCA, vol. 86, pp. 331-332, (1991).

*Primary Examiner*—David Brunsman
*Attorney, Agent, or Firm*—M. Howard Silverstein; John D. Fado; Joseph A. Lipovsky

[57] ABSTRACT

Chromium containing protein materials are treated by processes which include the steps of: combining the material to be treated with sufficient water to effect the solubilization of the gelable protein recovered therefrom, and an alkali additive. The mixture is thereafter held at a temperature of from about 60° C. to about 85° C. for a period of time of from about 0.5 hour to about 8 hours. The mixture is then filtered to remove the aqueous phase, which contains solubilized gelable protein. Subsequently, water is again added to the resultant chrome-containing proteinaceous cake and at least one enzyme is utilized to hydrolyze the remaining protein thus producing a product containing solubilized partially hydrolyzed protein and insoluble chromium. After separation, the chrome in the insoluble residue may be recycled into the pickling or tanning process, and the essentially chrome-free protein components may be used as ingredients in feeds, fertilizers, and cosmetics. The processes of the present invention are used to particular advantage to treat wastes from the leather tanning industry including blue stock, chrome shavings, chrome buffing dust, chrome cakes and chrome sludges.

19 Claims, No Drawings

ENZYMATIC PROCESSING OF MATERIALS CONTAINING CHROMIUM AND PROTEIN

This application is a continuation-in-part of U.S. patent application Ser. No. 07/476,843, filed Feb. 8, 1990 now U.S. Pat. No. 5,094,946.

FIELD OF THE INVENTION

This invention relates to the recovery of high molecular weight protein and chromium from chromium-containing leather waste.

BACKGROUND OF THE INVENTION

More than 95% of the leather manufactured in the U.S. is chrome tanned. Disposal of solid chrome wastes from the tanning process has become an increasingly serious problem to the leather industry. Chrome tanning generates approximately 54,000 metric tons of chrome waste annually in the U.S., about half in the form of chrome shavings. Sanitary landfills are reluctant to accept chromium-containing waste because of the potential for ground water contamination by toxic chromium compounds.

Chrome effluent from the bluing stage of leather tanning can usually be treated and then reused in the pickling or tanning process. Little, however, has been done with solid chrome shavings other than pressing them to form sheet-like products, or possibly hydrolyzing the shavings for chromium recovery.

Several Studies [Aunstrup et al., Brit. Pat. 1,243,784 (1968); Braeumer et al., Ger. Offen. 2,705,671 (1978); Leder- und Hautemarkt. Gerbereiwissenschaft und Praxis 30:100 (1978); Bronowski et al., Leder 30:8 (1979); Sauer et al., Leder- und Hautemarkt. Gerbereiwissenschaft und Praxis 36:70 (1984); Iliskovic et al., Koza Obuca 34(6):130 (1985)] have revealed that waste products from fleshing and beaming operations can be treated with enzymes at low temperatures for short periods of time to give products that have commercial value and/or are acceptable for disposal into municipal sewage systems. In contrast, previously disclosed procedures for treating solid chrome waste products usually are time-consuming or require boiling of the chrome wastes before enzymatic treatment [Suseela et al., Leder 34:82 (1983); 37:45 (1986); Parvathi et al., Leather Sci. 31:236 (1984); 33:8, 303 (1986); Monsheimer et al., Ger. Offen. 2,643,012 (1978); Hafner et al., Ger. (East) DD 212,983 (1984); DD 243,715 (1987)). Furthermore, in these processes, chromium is frequently dissolved and becomes difficult to separate from the hydrolyzed protein.

Heidemann [J. Am. Leather Chemists Assoc., 86:331-333 (1991)] proposes the use of proteolytic enzymes for better decomposition of chrome shavings after first boiling the shavings with calcium hydroxide. A minimum of about 1% enzyme is required and the protein hydrolysates are taught as being removed only after the enzymatic reaction.

SUMMARY OF THE INVENTION

We have now surprisingly discovered that with utilization of appropriate additives and reaction parameters (e.g., pH, temperature and treatment time) materials containing both chromium and protein (e.g., chrome waste from the leather industry) may be treated in a two step process at moderate temperatures for a short period of time to achieve solubilization of protein without miminal solubilization of the chromium. A reduction in enzyme consumption and an increase in the quality of the protein component recovered is achieved by adding the enzyme to partially denatured chrome-containing proteinaceous material after such material is first reacted with alkali and the resultant solubilized gelable proteins are removed. Upon addition of the enzyme, the remaining protein, is solubilized through hydrolysis and may be separated from the insoluble chromium. The chromium may then be recycled into the pickling or tanning process. The essentially chrome-free protein components are useful as ingredients in feeds, fertilizers, cosmetics, or may simply be treated as sanitary sewage.

In accordance with our discovery, it is an object of the instant invention to avoid the heating of chrome wastes to the high temperatures required in the aforementioned prior art, and thereby reducing the amount of time and energy required in the process.

It is another object of the invention to provide a process which is far more economical and commercially feasible than the prior art processes, by virtue of the aforementioned avoidance of high temperatures.

It is another object of the present invention to provide processes for converting chromium-containing materials into useful products.

It is also an object of the invention to provide a novel source of chromium for recycling into the pickling and/or tanning process.

It is another object of the present invention to provide such processes which are far more economical, and avoid chromium disposal problems, by virtue of the aforementioned recycling.

Another object of the invention is to provide a source of protein that can be isolated and purified for incorporation into a variety of products.

It is a further object of this invention to reduce enzyme utilization and to allow for the recovery of a gelable protein by adding the enzyme after the protein component solubilized through the alkali denaturation of collagen is removed.

It is a further object of the invention to avoid the possible risk of contaminating the environment with toxic chromium compounds that might result from the disposal of chrome wastes from the leather industry.

Other objects and advantages of this invention will become readily apparent from the ensuing description.

DETAILED DESCRIPTION OF THE INVENTION

Material to be treated in accordance with the present invention may contain chromium in either insoluble or solubilized form. Insoluble chrome wastes contemplated for treatment by the processes of the present invention include materials such as blue stock, chrome shavings, chrome buffing dust, chrome sludges and chrome cakes that result from effluent recycling. In the present specification and claims, the term "chrome shavings" is intended to have its usual and typical meaning in the leather industry—i.e., referring to pieces of animal hide complexed with chromium (including both protein and chromium) produced during chrome tanning of animal hide.

In accordance with the present invention, the chrome-containing proteinaceous materials are to be treated in a two step process involving the alkali denaturation of collagen and the enzymatic hydrolysis of non-solubilized protein. The chrome-containing proteinaceous material is first combined with sufficient water to effect the solubilization of the gelable protein recovered therefrom, this amount preferably being sufficient to produce a mixture having from about 75 weight % water to about 95 weight % water (most preferably from about 77 wt. % water to about 91 wt. % water).

In accordance with a first embodiment of the instant invention the material to be treated in the first step is also combined with an alkali additive which includes one or more of: (1) calcium oxide; (2) calcium hydroxide; and (3) one or more calcium salt in combination with one or more of sodium hydroxide, potassium hydroxide, sodium carbonate and potassium carbonate. The aforementioned additive is utilized in order to both adjust the pH and to provide alkali earth ions which are a cofactor for the enzymes utilized in the hydrolysis step. The additive is added in an amount sufficient to bring the pH of the mixture into the range of from about 8 to about 12 (preferably from about 10 to about 11); this amount ranging from about 1 weight % to about 8 weight % of the proteinaceous solids. This pH range is important for maintainence of the chrome in an insoluble state. Subsequently the mixture, which now contains the proteinaceous material to be treated, water and alkali additive, is held at a temperature of from about 60° C. to about 85° C. (more preferably from about 68° C. to about 72° C.) for a period of time from about 0.5 hour to about 8 hours (more preferably from about 5 hours to about 6 hours). At temperatures significantly below about 60° C. the collagen does not denature to the degree necessary for rendering the protein sufficiently susceptible to enzyme hydrolysis. At temperatures significantly above about 85° C. the process, while workable, becomes unattractive due to unnecessary energy costs. The aforementioned period of time is sufficient for pH and temperature stabilization, collagen denaturation and the entry of gelable large molecular weight proteins, previously entrained with the chromium-collagen complex, into aqueous solution. The reaction mixture is then separated by means which include gravitational settling, filtration or centrifugation with the large molecular weight proteins recovered in the aqueous phase and the chrome-containing proteinaceous solids being utilized in the second reaction step (enzymatic hydrolysis).

In accordance with a second embodiment of the present invention, in addition to being combined with the aforementioned proportion of water, the material to be treated is in the first step also combined with an alkali additive which includes one or more of: (1) magnesium oxide, (2) magnesium hydroxide; and (3) one or more magnesium salt in combination with one or more sodium hydroxide, potassium hydroxide, sodium carbonate and potassium carbonate. The alkali additive is added in an amount sufficient to bring the pH of the mixture into the range of from about 8 to about 12 (preferably from about 9 to about 11); this amount ranging from about 1 weight % to about 10 weight % of the proteinaceous solids. This pH range is important to the present invention for the same rationale set forth regarding the embodiment utilizing calcium compounds. More specifically, when the additive consists essentially of one or more of magnesium oxide or magnesium hydroxide, it is most preferred to utilize an amount of additive sufficient to bring the pH of the mixture into the range of from about 8.9 to about 9.1. Also, when the additive includes one or more of magnesium oxide or magnesium hydroxide and one or more of calcium oxide or calcium hydroxide, it is most preferred to utilize an amount of additive sufficient to bring the pH of the mixture into the range of from about 9.2 to about 10.4. Utilization of magnesium oxide in combination with sodium hydroxide is of particular advantage because magnesium catalyzes the reaction more efficiently than calcium, and substitution of sodium hydroxide for some magnesium makes the process more economical. When the additive includes magnesium oxide in combination with sodium carbonate, it is most preferred to utilize an amount of additive sufficient to bring the pH of the mixture into the range of from about 9 to about 10. The aforementioned additive not only serves to adjust the pH of the mixture, but also provides magnesium which is a cofactor for the enzymes. Subsequently, the mixture of the material to be treated, water and additive is held at a temperature of from about 60° C. to about 85° C. (more preferably from about 68° C. to about 72° C.) for a period of time from about 0.5 hour to about 8 hours (preferably from about 5 hours to about 6 hours). After the collagen has been denatured, the reaction mixture is then filtered resulting in a cake of chrome-containing proteinaceous solids and an aqueous filtrate containing gelable proteins. The proteins may be recovered by any of a variety of conventional techniques.

In the second process step, the chrome-containing proteinaceous cake, which is the residue from the first step is again combined with water; the quantity of which is sufficient to allow for the essentially complete hydrolysis of the remaining proteins, this amount preferably being sufficient to produce a mixture having from about 33 weight % water to about 75 weight % water (most preferably from about 45 weight % to about 55 weight %). If necessary the pH of the mixture is adjusted by the inclusion of sufficient acid or alkali additive so as to maintain appropriate conditions for enzyme activity and chrome insolubility. Usable acids include those compounds capable of lowering solution pH upon their inclusion. A non-limitative list of those envisioned for use with the invention include hydrochloric acid, sulfuric acid, acetic acid, formic acid and carbon dioxide. The mixture is then agitated with at least one enzyme specific for the hydrolysis of the protein being added in an amount ranging from about 0.01 weight % to about 0.50 weight % (preferably 0.05 weight % to about 0.10 weight %) of the proteinaceous solids.

The present invention may employ any of a variety of heat- and alkali-stable proteolytic enzymes. Examples include enzymes having the essential characteristics of the proteases that are available commercially under the name ALCALASE TM (optimal activity at 550°–650° C. and pH 8.3–9.0, Novo Laboratories, Inc., Danbury, Conn.); and proteases having the essential enzymatic characteristics of those available commercially under the names ENZECO TM ALKALINE PROTEASE-L (optimal activity at 50°–70° C. and ph 7.0–11.0, Enzyme Development Div., Biddle Sawyer Corp., New York, N.Y.); ESPERASE TM (Novo Laboratories, supra); and SAVINASE TM (Novo Laboratories, supra). Of course, any heat- and alkali-stable protease that is useful in hydrolyzing proteins from chrome wastes may be utilized.

The conditions of enzyme treatment, including the enzyme concentration and the time and temperature of reaction, are selected to achieve substantially complete hydrolysis of proteins from the chrome substrate without solubilizing the chrome. It is preferred to carry out the hydrolysis under agitation at a pH of from about 8 to about 12 (most preferably from about 8.3 to about 9.3), for a period of time from about 1 minute to about 5 hours (most preferably from about 2 hours to about 3 hours), and at a temperature of from about 25° C. to about 75° C. (most preferably from about 68° C. to about 72° C.).

After completion of the enzymatic hydrolysis, an aqueous fraction containing active enzyme and solubilized protein hydrolyzate (containing less than about 1 ppm chrome) may be separated from the insoluble chromium containing residue by any suitable means, including for example: gravitational settling, filtration or centrifugation. This aqueous fraction may be optimally recycled as an enzyme source in the process. The protein hydrolyzate may be recovered by any of a variety of conventional techniques, and utilized in feeds, fertilizers or cosmetics, or may simply be treated as sanitary sewage. Similarly, chromium can be recovered from the insoluble residue by any conventional procedure, such as solubilizing the separated insoluble chromium with an acid (e.g., sulfuric acid). The chromium sulfate in solution may be used directly in the pickle stage of hide processing or it may be precipitated, dried and used to make up the tan solution. Clearly, this recycling of the chrome is of tremendous significance as it both provides chrome used in the tanning and pickling, and eliminates the need for any chrome disposal. Because useful products can be recovered from both the soluble fraction and the insoluble residue, these products are of course important assets to the inventive processes.

The following examples are presented only to further illustrate the invention and are not intended to limit the scope of the invention which is defined by the claims.

EXAMPLE 1

The purpose of this example is to illustrate the effects of: the utilization of magnesium oxide to extract a high molecular weight protein from chrome shavings, and the utilization of an alkaline-stable proteolytic enzyme to hydrolyze the remaining protein attached to the chrome. 100 parts by weight of chrome shavings were suspended in 620 parts by weight water. To the sample was added 6 weight percent magnesium oxide. The sample was agitated for 330 minutes at 71° C. The warm solution was filtered and 47% of the available protein was recovered. The residue from the filtration was returned to the reaction vessel and 50 parts by weight of water was added. The sample was agitated at 71° C. for 30 minutes. 0.10 weight percent of Alcalase TM was added and the sample was agitated at 71° C. for 210 minutes. The solution was filtered and a recyclable chrome product was recovered as well as a low molecular weight hydrolyzed protein.

EXAMPLE 2

The purpose of this example is to illustrate the effects of: the utilization of magnesium oxide and sodium hydroxide to extract a high molecular weight protein from chrome shavings, and the utilization of an alkaline-stable proteolytic enzyme to hydrolyze the remaining protein attached to the chrome. 100 parts by weight of chrome shavings were suspended in 500 parts by weight water. To the sample was added 3 weight percent magnesium oxide and 3 weight percent sodium hydroxide. The samples were agitated for 360 minutes at 71° C. The warm solution was filtered and 65% of the available protein was recovered. The residue from the filtration was returned to the reaction vessel and 200 parts by weight of water was added. The sample was agitated at 71° C. for 60 minutes. 0.10 weight percent of Alcalase TM was added and the sample was agitated at 71° C. for 300 minutes. The solution was filtered and a recyclable chrome product was recovered as well as a low molecular weight hydrolyzed protein.

EXAMPLE 3

The purpose of this example is to illustrate the effects of: the utilization of magnesium oxide and sodium hydroxide to extract a high molecular weight protein from chrome shavings, and the utilization of a smaller amount of an alkaline proteolytic enzyme to hydrolyze the remaining protein attached to the chrome. 100 parts by weight of chrome shavings were suspended in 620 parts by weight water. To the sample was added 3.7 weight percent magnesium oxide and 3.7 weight percent sodium hydroxide. The sample were agitated for 330 minutes at 71° C. The warm solution was filtered and 65 percent of the available protein was recovered. The residue from the filtration was returned to the reaction vessel and 100 parts by weight of water was added. The samples were agitated at 71° C. for 30 minutes. 0.05 weight percent of Alcalase TM was added and the samples were agitated at 71° C. for 210 minutes. The solution was filtered and a recyclable chrome product was recovered as well as low molecular weight hydrolyzed protein.

The foregoing detailed descriptions and examples are given merely for purposes of illustration. Modification and variation may be made therein without departing from the spirit and scope of the invention.

We claim:

1. A method comprising:
   A) combining chromium-containing proteinaceous solids with: (a) sufficient water to effect the solubilization of the gelable protein recovered in step (C), and (b) an alkali additive in an amount sufficient to bring the pH of the mixture into the range of from about 8 to about 12;
   B) holding said mixture at a temperature of from about 60° C. to about 85° C. for about 0.5 hours to about 8 hours for the purpose of denaturing the collagenous protein and solubilizing the gelable proteins therein;
   C) separating the aqueous phase from said mixture for the purpose of retrieving said gelable protein;
   D) adding to the residue of said mixture: (a) at least one enzyme both specific for and in sufficient quantity for hydrolysis of the remaining proteins, (b) sufficient water to allow for essentially complete hydrolysis of the remaining proteins and, (c) sufficient acid or alkali additive so as to maintain pH conditions appropriate for enzyme activity and chrome insolubility; and
   E) holding the mixture at a temperature of from about 25° C. to about 75° C. for about 1 minute to about 5 hours for the purpose of producing a product containing solubilized hydrolyzed protein and insoluble chromium.

2. The method of claim 1 wherein the chromium-containing proteinaceous solids are selected from the group consisting of blue stock, chrome shavings, chrome buffing dust, chrome cakes and chrome sludges.

3. The method of claim 1 wherein the amount of water combined with said chromium-containing proteinaceous solids in step (A) is sufficient to produce a mixture having from about 75 weight % water to about 95 weight % water.

4. The method of claim 1 wherein the amount of alkali additive combined with said chromium-containing proteinaceous solids is from about 1 weight % to about 10 weight % based on the weight of said solids.

5. The method of claim 1 wherein said alkali additive includes one or more compounds selected from the group consisting of calcium oxide, calcium hydroxide, magnesium oxide, magnesium hydroxide, sodium hydroxide, sodium carbonate, potassium hydroxide, potassium carbonate, and mixtures thereof.

6. The method of claim 1 wherein the temperature utilized in the collagen denaturation of step (B) is from about 68° C. to about 72° C.

7. The method of claim 1 wherein the time required for the collagen denaturation of step (B) is from about 5 hours to about 6 hours.

8. The method of claim 1 wherein the separation of step (C) is carried out by gravitational settling, filtration and centrifugation.

9. The method of claim 1 wherein the amount of enzyme utilized in step (D) is from about 0.01 weight % to about 0.50 weight % based on the weight of said remaining non-aqueous phase.

10. The method of claim 9 wherein the amount of enzyme utilized is from about 0.05 weight % to about 0.10 weight %.

11. The method of claim 1 wherein the amount of water combined with the remaining non-aqueous phase of step (D) is sufficient to produce a mixture having from about 33 weight % water to about 75 weight % water.

12. The method of claim 1 wherein the acid or alkali additive of step (D) includes one or more compounds selected from the group consisting of hydrochloric acid, sulfuric acid, calcium oxide, calcium hydroxide, magnesium oxide, magnesium hydroxide, sodium hydroxide, sodium carbonate, potassium hydroxide and potassium carbonate.

13. The method of claim 1 wherein the pH of step (D) is maintained within the range of from about 8 to about 12.

14. The method of claim 13 wherein the pH of step (D) is maintained within the range of from about 8.3 to about 9.3.

15. The method of claim 1 wherein the temperature utilized in the enzymatic hydrolysis of step (E) is from about 68° C. to about 72° C.

16. The method of claim 1 wherein the time required for the enzymatic hydrolysis of step (E) is from about 2 hours to about 3 hours.

17. The method of claim 1 which includes the further step of separating the insoluble chromium from the product of step (E).

18. The method of claim 17 wherein said separation is by one or more of gravitational settling, filtration and centrifugation.

19. The method of claim 1 wherein the proteins recovered contain less than about 1 ppm. chromium.

* * * * *